United States Patent [19]

Higuchi et al.

[11] Patent Number: 4,684,740

[45] Date of Patent: Aug. 4, 1987

[54] PRODUCTION OF 2,6-BIS (4-HYDROXY-3,5-DIMETHOXYPHENYL-3,7-DIOXABICYCLO (3.3.0) OCTANE

[75] Inventors: Takayoshi Higuchi, Kyoto; Mitsuhiko Tanahashi, Uji; Motoo Mastukura, Tokyo, all of Japan

[73] Assignee: Jujo Paper Co., Ltd., Tokyo, Japan

[21] Appl. No.: 840,757

[22] Filed: Mar. 18, 1986

[30] Foreign Application Priority Data

Mar. 22, 1985 [JP] Japan .................................. 60-58079

[51] Int. Cl.$^4$ .......................................... C07D 493/04
[52] U.S. Cl. ..................................... 549/464; 162/121
[58] Field of Search ........................... 549/464; 162/21

[56] References Cited

FOREIGN PATENT DOCUMENTS 1096374  2/1981  Canada .

OTHER PUBLICATIONS

Omori and Sakakibara, J. Wood Research Society, vol. 17, pp. 464–467 (1971).
Sudo and Sakakibara, J. Wood Research Society, vol. 19, No. 4, pp. 165, 169 (1973).
Tanahashi et al., Wood Research, vol. 69, pp. 36–51 (1983).
Wood Research, vol. 32, No. 12, pp. 39–47 (1983).
Tanahashi et al., Wood Research, vol. 61, pp. 44–53, (1976).
Bardet et al., Sven. Papperstidn. vol. 88 (6), R61–R67, (1985), Chem. Abstracts, vol. 103, 388 (1985).
Draganova et al., Cellul. Chem. Technol. vol. 14(4), pp. 469–477 (1980), Chem. Abstracts, vol. 94, 5077.
Nimz et al., Chem. Ber., vol. 98, pp. 538–539, (1965).

*Primary Examiner*—Henry R. Jiles
*Assistant Examiner*—Bernard I. Dentz
*Attorney, Agent, or Firm*—Sherman & Shalloway

[57] ABSTRACT

This invention discloses a process for producing 2,6-bis (4-hydroxy-3,5-dimethoxyphenyl)-3,7-dioxabicyclo [3.3.0] octane, i.e. syringaresinol and stereo-isomers thereof, from plants which contain lignin with syringyl unit. The process comprises heating plant under pressure in hydrous condition, and then quickly discharging them therefrom into an environment at atmospheric pressure so as to explode into pieces and subjecting the fine pieces to extraction with organic solvent such as methanol and acetone or an alkaline solution such as sodium hydroxide and purification. Syringaresinols are useful like ginseng as a tonic.

13 Claims, No Drawings

PRODUCTION OF 2,6-BIS (4-HYDROXY-3,5-DIMETHOXYPHENYL-3,7-DIOXABICYCLO (3.3.0) OCTANE

FIELD OF THE INVENTION

This invention relates to a process for yielding 2,6-bis(4-hydroxy-3,5-dimethoxyphenyl)-3,7-dioxabicyclo[3.3.0] octane, i.e. syringaresinol and stereo-isomers thereof (hereinafter referred to as syringaresinols) efficiently in good yield.

DESCRIPTION OF THE PRIOR ART

It is known that syringaresinols, classified into lignan, one of the plant components, is present in hardwoods and herbs together with their glucoside and that lignin, one of the main components of broad-leaf trees or herbs includes them. Recently it is recognized in our country that *Acanthopanax senticosus* is as effective in activating robustness and improving defense reaction of organisms as ginseng, which has so far been used as a medicinal herb. In this respect, mainly scientists of the Soviet Union have reported that syringaresinols and their glucoside are an active component of *Acanthopanax senticosus*. Despite the fact that the compound has been attracting so much attention as a new biologically active substance, nothing has been studied about their effective methods of production economically although only few studies have so far been reported on the experimental separation method for the sake of pure scientific interest.

Since syringaresinols are found to be present in broad leaf trees in the form of their glucoside as mentioned above, they can be obtained in association with many other compounds from an extractives of the stem or bark upon direct immersion in methanol. However, yields are generally as poor as 0.01% or less based on the whole weight of the subjected material. That is, even when the inner bark of *Liriodendron tulipifera*, which reportedly contains much syringaresinols, is subjected to extraction, their yield is about 0.5%, so that it may be about 0.02% at best based on the whole wood. In other words, this means there are contained a lot of impurities together with them; therefore, their purification needs many troublesome steps in their separation, with the result that their production cost cannot help remarkably increasing.

To make matters worse, the direct extraction gives rise to three different kinds of resinols very much alike in structure at the same time. That is, in the following structural formula (I), other than syringaresinol containing syringyl radical, in which $R_1$, $R_2$, $R_3$ and $R_4$ are equally $OCH_3$, there appear two other resinols: one pino resinol containing guaiacyl unit, in which $R_1$ and $R_3$ are $-OCH_3$ and $R_2$ and $R_4$ are $-H$ and the other medio resinol containing guaiacyl and syringyl unit, in which $R_1$, $R_2$ and $R_3$ are $OCH_3$ and $R_4$ is H in a mixed condition therewith. Therefore, in order to isolate pure syringaresinol from the mixture, much more sophisticated separation processes are required.

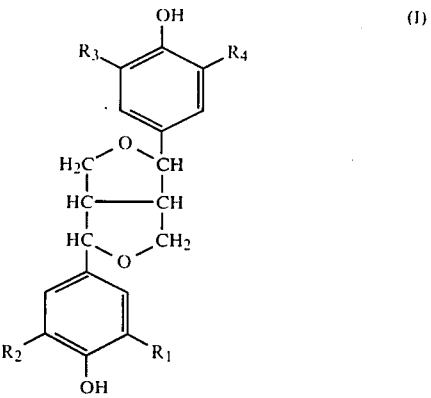

In herbs, a trace of syringaresinols are similarly found to be present in *Artimisia absinthum*, *Vinca major*, *Vinca rosea*, etc. Meanwhile, wood and herbs contain 20-30% and 15-25% of lignin respectively. In connection with this, it has been made clear that para-hydroxycinnamyl alcohols, a monolignol comprising a primary structural element in this case, are de-hydrogenated by an enzyme in plants so as to give phenoxy radical and their resonance hybrids form a variety of dilignols comprising a secondary structural element, as they radically polymerize among themselves and the dilignols further polymerize among themselves so as to give eventually a three-dimensional net-work structured polymer. As typical dilignols, arylglycerol-α-(or β)-arylether, phenyl coumaran, biphenyl and diarylpropane are known and the presence of resinols has also been recognized, but the amount of the resinols is less than that of the four former products. The composition of para-hydroxycinnamyl alcohols (monolignol) is different from one plant to another, consequently, resulting dilignols therefrom are different from each other in variety and amount. For example, with reference to the following structural formula (II), softwood lignin is composed almost entirely of coniferyl alcohol ($R_1=OCH_3$ and $R_2=H$); hardwood lignin is composed of coniferyl alcohol and sinapyl alcohol ($R_1=R_2=-OCH_3$) in the 1:1 ratio; grass lignin is composed of coniferyl, sinapyl and para-coumaryl alcohols ($R_1=R_2=-H$) in the 4.5:4.5:1 ratio. Syringaresinol is linked to a lignin macromolecule of hardwood or grass with ether linkage.

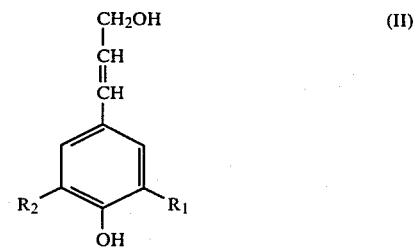

Hitherto, as a process for separating syringaresinol from lignin, there has been used special hydrolytic methods such as percolation with hot water [Chem. Ber.; 98, 538 (1965)] and digestion with dioxan-water solution [J. Wood Research Society: 17, 464 (1971)] or a hydrogenolysis method with metal catalyst such as copper oxide-chromium binary composite [J. Wood Research Society: 19, 165 (1973)]. However, these methods are useful only for the separation of syringaresinol from lignin for the purpose of studying its structural changes but almost meaningless as an industrial process on condition of commercialization.

Additionally, a few synthetic methods for producing syringaresinol on a laboratory scale have been repored but with any of them it is very difficult to collect a starting material in industrial scale; besides, synthetic steps up to the final product are very complicate. For these reasons, it can be said that they are also almost worthless presupposing commercialization.

SUMMARY OF THE INVENTION

Accordingly, it is an object of this invention to provide a process that can produce syringaresinols in an industrial scale, in place of the above mentioned experimental processes. The object of this invention can be accomplished by a production process of 2,6-(4-hydroxy-3,5-dimethoxyphenyl)-3,7-dioxabicyclo[3.3.0] octane, which is characterized in that plant containing lignin with syringyl unit are heated under pressure in an autoclave under a hydrous condition, quickly discharged thereof into a receiver under normal pressure and then subjected to extraction with an organic solvent or an alkaline solution.

DESCRIPTION OF THE PREFERRED EMBODIMENTS

In Wood Research (69, 36–51 (1983), Kyoto University) and Polymer Applicatives (32(12), 39–47 (1983)), the present inventors have reported that when water-containing wood chips are subjected to heat under high pressure and then depressurized quickly, wood tissues are easily disintegrated and defibrated to yield pulp. They thus showed this explosion process is very interesting as a new pulp-manufacturing process. In the process of their study, they have also found lignin decomposes into smaller molecules which are soluble in an organic solvent. That is, as a result of investigation in detail, it became clear that when hardwood chips are subjected to extract with an organic solvent after being treated at an elevated temperature under high pressure and then depressurized quickly the extractives contain plenty of syringaresinols; thus, the inventors have accomplished the invention.

Concretely, this invention provides a new production process of syringaresinols which comprises: heating plant, such as hardwood chips containing lignin with syringye unit under pressure in an autoclave at a hydrous condition, quickly discharging them thereof into a receiver under atmospheric pressure, crushing them into small pieces and subjecting them to an organic solvent or an alkaline solution extraction followed by purification. According to this invention, syringaresinols can be obtained economically from cheap and accessible wood in a very good yield.

The syringaresinol production process of this invention can fundamentally be divided into three major steps: heating hydrous plant with saturated steam under high pressure, instantly discharging them thereof at atmospheric pressure, and after crushing, subjecting them to an organic solvent or an alkaline solution extraction and purification. Accordingly, the steps of this invention will be described in more detail.

In this invention, as long as they contain lignin with syringyl unit as one of their components, any such plant as hardwood, bamboos, straws, cottonseed shell, coconut shell and almond shell are available as a starting material. When the lignin content is small, the content of impurities is much in contrast thereto; this makes the purification process more difficult and follows economical disadvantage; therefore, it is recommendable to use plant that contain not less than 5% by weight of Klason lignin based on their weight. It is also desirable for the plant materials to contain not less than 10% of moisture prior to the heat treatment under pressure in view of their uniform reaction and their uniform disintegration into fibrils. If not so initially, they can uniformly be moistened by condensed steam as heating steam is introduced into an autoclave. Therefore, if only the plant materials are not in an excessively dried condition, it is enough. Also, considering the easiness of handling and their crushability, the plants are preferably cut into chips or pieces not more than a few centimeters in size.

The plant are put in a jacketed autoclave; subsequently, the inside air is replaced with a low pressure steam of about 1–2 kg/cm$^2$. The autoclave is then wholly heated; saturated steam is introduced therein up to a desired pressure. The steam pressure used for this treatment is desirably in the range of from 10 to 40 kg/cm$^2$. If it is less than 10 kg/cm$^2$, the softening of the plant tissues, i.e. solubilization of hemicellulose into water by hydrolysis and depolymerization of lignin molecule, becomes insufficient and the yield of syringaresinols becomes less in consequence. The higher the temperature and the pressure applied, the faster the reaction rate is in general, which results in a higher yield of syringaresinols. However, the temperature and the pressure are preferably so high as to keep an active pressure inside an autoclave between 20 and 30 kg/cm$^2$ because the yield of syringaresinols reaches its highest level at 25 kg/cm$^2$. The reaction time can be reduced much more when more active pressure than the above is applied, but the yield of the product cannot be expected to increase any more. On the contrary, such over-heating and over-pressurizing as raising the active pressure over 40 kg/cm$^2$ is more likely to cause the carbonization of the plant; therefore, good care must be taken to avoid excessive pressure. A set of equipment capable of realizing such condition is expensive in general, but rather uneconomical for this use.

Meanwhile, the time to retain the temperature and the pressure so that syringaresinols can be obtained in the highest yield is at best 20 minutes at an active pressure of 25 kg/cm$^2$ and should not be more than 10 minutes at an active pressure of 30 kg/cm$^2$ although it depends on the kind of plant to be employed.

The plant thus heated under high pressure is discharged into a mufflered receiver at atmospheric pressure through a small pipe in a moment. In order to discharge instantly, it is desirable to use a device having excellent sealability such as a ball valve, a rotary valve and the like superior in air tightness. When the plant subjected to heating under high pressure is discharged in the manner described above, the plant is broken into pieces uniform in size by the action of the forces resulting from quick vaporization of high-temperature water placed under high pressure and the mechanical shock and/or friction between the plants themselves or between the plant and the tube wall resulting from the passage of the hydrous plant treated with the above method through the small tube. Hemicellulose in the uniformly broken plant is hydrolyzed and became water-soluble, and lignin depolymerizes and becomes an oily droplet. Further the both constituents have been exhausted out of the plant cellular membrane; therefore, lignin degradation product containing syringaresinol is very easily extracted with an organic solvent or an alkaline solution.

Syringaresinols, together with lignin degradation products, are extracted by soaking the crushed, moistened vegetable pieces in such organic solvents as methanol, dioxane, tetrahydrofuran, etc. or an alkaline solution as they are or after dispersing them in several-fold amount of water and filtering so as to remove water-soluble substances like sugars.

A residue that appears after the removal of the organic solvents from the extracted solution is a black solid, and lignin decomposition products are obtained for precipitate when the alkaline solution is acidified with the addition of acid. The purification of the residue or the precipitate may be carried out according to a conventional method, but with this a resulting product contains plenty of impurities. In order to obtain efficiently the pure objective products, it is preferable to purify components of the residue or precipitate soluble in ethers, esters, aromatic hydrocarbons or chlorine-substituted hydrocarbons.

Additionally, crushed, vegetable pieces which are freeze-dried or dried under reduced pressure can be subjected to extraction with ethers, esters, aromatic hydrocarbons or chlorine-substituted hydrocarbons. A solid product containing 5-15% of syringaresinols appears when solvent is removed from the extracted solution by distillation. The yield of the solid product is different from one plant to another used; however, in the case of hardwood, it is about 10-15% based on the weight of a dried material.

Recrystallizing or purifying the solid product according to various well-known chromatographic processes gives syringaresinols of high purity. The syringaresinols formed according to this invention are a mixture of syringaresinol and episyringaresinol; optically, they are a mixture of d- and l-isomers.

This invention has made it possible to yield a far greater amount of syringaresinols than they are contained in lignin or extractable components of a plant material used. The reason for this has to be clarified by further studies including model experiments; nonetheless, it can be considered as follows:

Lignin in plant depolymerizes into smaller molecule through a cleavage of arylglycerol-α-aryl ether and arylglycerol-β-aryl ether, the most essential units in lignin, by the catalytic action of activated water with high temperature and pressure and acetic acid resulting from the decomposition of acetyl groups in hemicellulose. In the process of the cleavage, one water molecule is eliminated from syringylglycerol-β-aryl ether represented by a structural formula (III) shown below. As a result, there forms a quinonemethide structure (IV). Subsequently, β-aryl ether linkage is cleavaged radically and there forms quinonemethide radical (V), which couples again in pairs so as to form a ring structure by which syringaresinols are built up. Side chains of the formed syringaresinol are chemically stable. Its aromatic ring is also stable because the ortho and para positions of phenolic hydroxy group are substituted; the phenolic hydroxy group is thus only a reaction site. Therefore, it seems that even if there forms a phenyl ether linkage, it immediately cleavages and syringaresinol formed as ever.

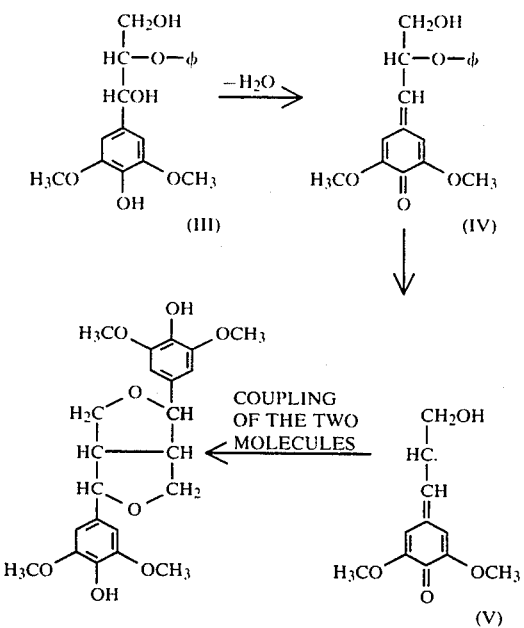

As having published in the 33rd meeting of Wood Research Society of Japan (see preceding; p. 283 (1983)), the present inventors have recognized by nuclear magnetic resonance spectrum that almost all arylglycerol-β-aryl ether linkages disappear in lignin degradation products after hardwood is subjected to explosion. Likewise, they have recognized that syringaresinols are produced in a 70-90% yield via an enzymatic dehydrogenating polymerization in vitro or an oxidizing dehydrogenative polymerization, which are typical radical reactions of sinapyl alcohol (see Wood Research; 61, 44–53 (1976). For the above reasons, it seems probable that under such condition as specified in this invention, syringylglycerol-β-allyl ether linkage contained in lignin cleavages as to form quinonemethide radical as shown by the structural formula (V), which couples again and their forms syringaresinol in plenty. Additionally, in the condition of this invention, syringaresinol is easy to change to episyringaresinol because the whole reaction system becomes acidic when heating is carried out under high pressure. Therefore, episyringaresinol produced in this invention might be a product derived from syringaresinol by way of the mechanism mentioned above.

According to this invention, cheap plant from broad leaf trees, bamboos, coconuts, etc. can be employed, so that syringaresinols can be produced in a very good yield. In addition, commercialization can be put into practice easily and high profitability is promising because both processes for crushing plant materials and for extraction with an organic solvent or an alkaline solution do not need complicated production equipment or operations.

This invention will be understood more readily with reference to the following examples; however, these examples are intended to illustrate the invention and are not to be construed to limit the scope of this invention.

EXAMPLE 1

Two hundred grams based on oven dry weight of *Fagus crenata* wood chips were charged in an autoclave with a capacity of 2 l and a pressure limit of 40 kg/cm² whose top was provided with a steam-inlet tube and an air-outlet tube and whose bottom was provided with a ball valved pipe leading to a muffled receiver. Each time the air-outlet tube was opened, a 2 kg/cm$^2$ saturated steam was introduced into the autoclave for 2-3 seconds in order to purge the inside air. This cycle was repeated three times. After the air was replaced with steam, the air-outlet tube was closed; the autoclave and its jacket were filled with a 30 kg/cm$^2$ saturated steam and then the material wood chips were heated rapidly under high pressure. The inside maximum temperature attained 235° C. After that, the introduction of the steam was stopped immediately; the autoclave was kept standing as it was for 8 minutes. The ball valve was opened. The wood chips were discharged from the autoclave into a receiver in a very short period of time, say almost in a moment. The inside of the receiver was rinsed with water to collect the crushed wood material as it was dispersed in water, which was then topped up to 3 l. The solution was stirred and filtered with the aid of an aspirator. Another two cycles of such filtration were conducted and then residue, part of the crushed wood, was dispersed in 2 l of methanol, which was stirred and filtered. The same operation was repeated two more times. All of the methanol used for the three cycles of filtration were collected, condensed and dried up. An extract from the methanol weighed 52 g, which was dissolved in 200 ml of dioxane. The dioxane solution was added dropwise to 2 l of ethyl ether with stirring. Precipitate were filtered out and only an ether-soluble fraction was collected. Thirty grams of a solid residue remained after the removal of the ether by distillation.

The solid product was charge into a column filled with silica gel (#C-200), a product of Wako Chemicals Co., Ltd.). Elution was carried out by the use of a methanol-chloroform 1:99 (by volume) mixed solvent and a portion including syringaresinols was collected under the monitoring with the silica gel thin layer chromatography. After the solvent was removed from the eluate, 3 g of crude crystal containing syringaresinol was obtained. Upon recrystallization of the crude crystal, 2.5 g of crystal composed only of syringaresinol and episyringaresinol were obtained, which showed peaks in agreement with each authentic corresponding sample when subjected to high performance liquid chromatography.

EXAMPLE 2

Two hundred grams of dried pieces of *Phyllostachys pubescens* were charged into the same autoclave as used in Example 1. The bamboo pieces were treated with a 28 kg/cm$^2$ saturated steam at 230° C. for 10 minutes according to the similar procedure in Example 1 and then caused to quickly discharge therefrom into a receiver under the atmospheric condition.

A solution containing treated, broken bamboo pieces was subjected to extraction in the same way as in Example 1 with the use of water and methanol. It gave 47 g of an extract after the drying of the methanol. The extract was dissolved in a 200 ml mixture solvent composed of dichloroethane and ethanol (2:1 by volume) and added dropwise to ethyl ether; thus, 22 g of an ether-soluble product were obtained.

A column filled with silica gel (#C-200, a product of Wako Chemicals Co., Ltd.) was charged with the product, which was eluated with a mixture solvent composed of benzene and ethyl acetate (2:1 by volume). Under the monitoring with the silica gel thin layer chromatography, episyringaresinol and then syringaresinol were collected from the eluate. After removing the solvent from the eluation, 1.7 g of episyringaresinol and 1.3 g of syringaresinol were obtained in a crude crystal form. Upon their recrystallization with a methanol-chloroform mixture solvent, 1.5 g of episyringaresinol and 0.9 g of syringaresinol were yielded in a pure crystal form. The NMR spectrum and the melting point of these products agreed with these of authentic compounds.

EXAMPLE 3

Two hundred grams of cottonseed shell were treated with a 25 kg/cm$^2$ saturated steam on condition that the maximum temperature was about 220° C. and the time of retaining the maximum temperature was 12 minutes in the same autoclave according to the same procedure in Example 1, from which resulted a solution containing crushed cottonseed shell. When the solution was extracted with water and methanol, there formed 94 g of an extract. After the similar treatment as in Example 1, 1.8 g of crystal composed only of syringaresinol and episyringaresinol resulted from the extract.

EXAMPLE 4

Two hundred grams of white birch (*Betula tauschii*) wood chips were treated with a 28 kg/cm$^2$ saturated steam on condition that the maximum temperature was 230° C. and the time of retaining the maximum temperature was 8 minutes in the same autoclave according to the same procedure in Example 1, from which resulted a solution in which crushed white birch wood dispersed. The residue which was obtained from the solution filtration was put to extraction with water in the same way as in Example 1 and filtered. A residue after the filtration was dispersed in 3 l of 1% NaOH aqueous solution, extracted with stirring and filtered. A similar alkali-extraction was repeated again. The solution resulting from the two cycles of alkali-extraction was added and its pH was made 4 by 10% hydrochloric acid. A precipitate thus formed was filtered, rinsed with water and dried; then, there formed 51 g of a solid. The solid extract was dissolved in 300 ml of 1,2-dichloroethane and ethanol (2:1) mixture solvent, which was added dropwise to isopropyl ether in the same way as in Example 1; as a result, 28 g of an isopropyl ether-soluble product were obtained. The isopropyl ether-soluble product was treated according to the same condition and procedure as in Example 2, with the result that 1.3 g of syringaresinol and 0.9 g of episyringaresinol were obtained respectively in a pure crystal form.

We claim:

1. A process for the production of 2,6-bis(4-hydroxy-3,5-dimethoxyphenyl)-3,7-dioxabicyclo(3.3.0) octane, which comprises heating plants containing lignin with syringyl unit under pressure in an autoclave in a hydrous condition, quickly discharging the heated, pressurized plants into a receiver at atmospheric pressure, subjecting the discharged plants to extraction with an organic solvent or an alkaline solution and recovering the 2,6-bis(4-hydroxy-3,5-dimethoxyphenyl)-3,7-dioxabicyclo(3.3.0) octane from the resulting extract.

2. A production process of 2,6-bis(4-hydroxy-3,5-dimethoxyphenyl)-3,7-dioxabicyclo[3.3.0] octane as set forth in claim 1, which is characterized in that said plants are hardwoods or herbs.

3. A production process of 2,6-bis(4-hydroxy-3,5-dimethoxyphenyl)-3,7-dioxabicyclo[3.3.0] octane as set forth in claim 2, which is characterized in that said plants are fruit skins of broad-leaf trees or seed crusts of herbs.

4. A production process of 2,6-bis(4-hydroxy-3,5-dimethoxyphenyl)-3,7-dioxabicyclo[3.3.0] octane as set forth in claim 1, which is characterized in that said organic solvent is a solvent selected from the group consisting of an alcohol, an ether, a ketone, an ester, a chlorine-substituted hydrocarbon and an aromatic hydrocarbon.

5. A production process of 2,6-bis(4-hydroxy-3,5-dimethoxyphenyl)-3,7-dioxabicyclo[3.3.0] octane as set forth in claim 1, which is characterized in that a saturated steam is used for heating said plant under pressure.

6. A production process of 2,6-bis(4-hydroxy-3,5-dimethoxyphenyl)-3,7-dioxabicyclo[3.3.0] octane as set forth in claim 5, which is characterized in that a saturated steam of 10–40 kg/cm$^2$ is used for heating said plant under pressure.

7. A production process of 2,6-bis(4-hydroxy-3,5-dimethoxyphenyl)-3,7-dioxabicyclo[3.3.0] octane as set forth in claim 5, which is characterized in that a saturated steam of 20–30 kg/cm$^2$ is used for heating said plants under pressure.

8. The process of claim 1 wherein the plants contain at least 5% of Klason lignin and at least 10% of moisture prior to the heating step.

9. The process of claim 1 which further comprises dispersing the discharged plants in water and filtering the dispersion to remove water-soluble substances from the plants prior to subjecting the discharged plants to extraction.

10. The process of claim 9 wherein the steps of extracting and recovering comprise extracting the plants after removal of water-soluble substances with methanol, to obtain a methanol extract, removing methanol from the extract to obtain a methanol soluble residue, adding the residue to ether to extract ether soluble matter from the residue, removing ether from the ether extract, and recovering 2,6-bis(4-hydroxy-3,5-dimethoxyphenyl)-3,7-dioxabicyclo(3.3.0) octane.

11. The process of claim 10 wherein the product dioxabicyclo octane is recovered by crystallization and recrystallation.

12. The process of claim 1 wherein the heated plants are maintained under pressure in the autoclave for a time sufficient to maximize the yield of the product dioxabicyclo octane.

13. The process of claim 7 wherein the plants are maintained under steam pressure for about 10 minutes.

* * * * *